(12) United States Patent
Murty et al.

(10) Patent No.: US 9,333,175 B2
(45) Date of Patent: May 10, 2016

(54) CONTROLLED RELEASE LEVETIRACETAM FORMULATIONS AND METHODS FOR PRODUCING THE SAME

(75) Inventors: Mummini Aruna Murty, Morgantown, WV (US); Boyong Li, Morgantown, WV (US)

(73) Assignee: Mylan Inc., Canonsburg, PA (US)

( * ) Notice: Subject to any disclaimer, the term of this patent is extended or adjusted under 35 U.S.C. 154(b) by 526 days.

(21) Appl. No.: 12/816,620

(22) Filed: Jun. 16, 2010

(65) Prior Publication Data

US 2011/0311627 A1 Dec. 22, 2011

(51) Int. Cl.
*A61K 9/20* (2006.01)
*A61K 9/22* (2006.01)
*A61K 9/28* (2006.01)
*A61K 31/4015* (2006.01)

(52) U.S. Cl.
CPC ............ *A61K 9/2027* (2013.01); *A61K 9/2054* (2013.01); *A61K 9/2866* (2013.01); *A61K 31/4015* (2013.01)

(58) Field of Classification Search
None
See application file for complete search history.

(56) References Cited

U.S. PATENT DOCUMENTS

| | | | | |
|---|---|---|---|---|
| 5,185,159 | A * | 2/1993 | Aubert et al. | 424/489 |
| 6,309,663 | B1 * | 10/2001 | Patel et al. | 424/450 |
| 2005/0106251 | A1 * | 5/2005 | Langridge et al. | 424/470 |
| 2005/0202088 | A1 * | 9/2005 | Hanshermann et al. | 424/471 |
| 2006/0165796 | A1 | 7/2006 | Kshirsagar et al. | |
| 2007/0092569 | A1 * | 4/2007 | Kshirsagar et al. | 424/472 |
| 2008/0014264 | A1 | 1/2008 | Goffin et al. | |
| 2008/0014271 | A1 | 1/2008 | Goffin et al. | |
| 2009/0263481 | A1 * | 10/2009 | Patil et al. | 424/472 |

FOREIGN PATENT DOCUMENTS

| | | | |
|---|---|---|---|
| EP | 1473030 A1 | 11/2004 | |
| WO | 03007918 A1 | 1/2003 | |
| WO | WO 2009049642 A1 * | 4/2009 | ............. A61K 9/20 |
| WO | 2010026467 A2 | 3/2010 | |

OTHER PUBLICATIONS

Salbutamol Sulfate (Albuterol) Kinase Inhibitor, Datasheet [online], EnoGene Biotech Co., [retrieved on Aug. 4, 2015], retrieved from the Internet: <URL: www.enogene.com/uploads/b6671ecd284a357cb6c967e1ce85f653-1/files/E1KS2507.pdf>, p. 1.*
Clemedson, "Valproic acid and sodium valproate", Feb. 2007 [retrieved on Aug. 4, 2015], retrieved from the Internet: <URL: www.acutetox.eu/pdf_human_short/16-Sodium%20 valproate%20revised.pdf>, pp. 1-4.*
Pearnchob et al., "Dry polymer powder coating and comparison with conventional liquid-based coatings for EUDRAGIT RS, ethylcellulose and shellac", 2003, European Journal of Pharmaceutics and Biopharmaceutics, vol. 56, pp. 363-369.*
Gower et al., European Journal of Pharmacolgoy, 222; 193-203 (1992).
International Search Report and Written Opinion for Application PCT/US2011/039030 dated May 10, 2012.

* cited by examiner

*Primary Examiner* — Michael B Pallay
(74) *Attorney, Agent, or Firm* — Lerner David Littenberg Krumholz & Mentlik

(57) ABSTRACT

Pharmaceutical compositions in the form of tablets are disclosed including water-soluble active ingredients such as levetiracetam and a polymer component which primarily includes water-insoluble polymers comprising between 60% and 100% of the polymer component in the tablet core, preferably the entire polymer component in the tablet core. The pharmaceutical compositions can also include an extended-release coating including both water-soluble and water-insoluble polymers.

30 Claims, 3 Drawing Sheets

CONTROLLED RELEASE LEVETIRACETAM FORMULATIONS AND METHODS FOR PRODUCING THE SAME

FIELD OF THE INVENTION

The present invention relates to novel pharmaceutical compositions comprising water-soluble active ingredients. More particularly, the present invention relates to novel pharmaceutical compositions comprising levetiracetam.

BACKGROUND OF THE INVENTION

There has been much emphasis in the pharmaceutical industry on the development of extended or controlled release drugs of various kinds. Doing so permits greater time periods between dosages, greater patient compliance, and the like. In connection with various water-soluble active ingredients, however, the development of extended release drug formulations has been somewhat difficult. This is exacerbated by the ready dissolution of these drugs, thus making it far more difficult to control the release of these substances for administration in a smaller number of dosages, such as single daily doses or even greater time periods between dosages.

Among these water-soluble drugs one highly important such drug is levetiracetam.

Levetiracetam or (S)-(−)-alpha-ethyl-2-oxo-1-pyrrolidine acetamide, a laevorotatory compound, is disclosed as a protective agent for the treatment and the prevention of hypoxic and ischemic type aggressions of the central nervous system in European patent No. EP 0 162 036 B and has the following formula:

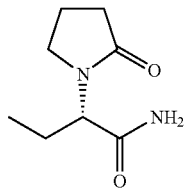

This compound is also effective in the treatment of epilepsy, a therapeutic indication for which it has been demonstrated that its dextrorotatory enantiomer (R)-(+)-alpha-ethyl-2-oxo-1-pyrrolidine acetamide completely lacks activity (A. J. Gower et al., Eur. J. Pharmacol., 222, 1992, 193-203).

Recent developments in the production of extended release tablets of such drugs include U.S. Patent Publication Nos. 2007/0092569 ("the '569 Publication"); 2006/0165796 ("the '796 Publication"); 2008/0014271 ("the '271 Publication"); and 2008/0014264 ("the '264 Publication"). Each of these publications is generally directed to extended release formulations of levetiracetam in which a tablet core is prepared which primarily comprises a water-soluble rate-controlling polymer, optionally including conventional excipients, binders and the like. These hydrophilic rate-controlling polymers are included in the core in amounts from about 1% w/w to about 50% w/w. It is further disclosed that these tablets can be coated with a hydrophobic water-insoluble polymer either alone or including a water-soluble polymer as a nonfunctional coating.

Similarly, the '271 Publication discloses another such extended release composition. In this case, the tablet core containing levetiracetam includes a hydrophilic matrix agent or water-soluble agent, which can be combined with inert and lipophilic matrix agents, some of which can be water-nondispersible agents. In all of the compositions disclosed in the '271 Publication, however, the hydrophilic matrix agent is an essential element in the core including the water-soluble drug component levetiracetam.

Since these drug compositions require the use of a water-soluble polymer in the core to attempt to control the drug release rate, this results in a rather unpleasantly bulky drug product for high dose drugs such as levetiracetam, thus interfering with patient compliance. Furthermore, the flexibility of these extended release drugs is hampered with only a single drug release controlling mechanism in the core. In addition, with a highly swellable hydrophilic polymer matrix in these compositions, release controlling coatings on the systems are not extremely effective.

Additional efforts have therefore been made to provide novel and more patient-friendly extended release drug formulations including water-soluble drugs such as levetiracetam.

SUMMARY OF TEE INVENTION

In accordance with the present invention, these and other objects have now been realized by the discovery of a pharmaceutical composition in the form of a tablet comprising a tablet core comprising a water-soluble active ingredient and a polymer component comprising a water-insoluble polymer comprising from between about 1 and 50 wt. % of the tablet core, and wherein the water-insoluble polymer comprises between about 60% and 100% of the polymer component. In a preferred embodiment, the polymer component consists essentially of the water-insoluble polymer.

In accordance with one embodiment of the pharmaceutical composition of the present invention, the composition includes an extended release coating surrounding the tablet core. Preferably, the extended release coating comprises a mixture of at least one water-insoluble polymer and at least one water-soluble polymer.

In accordance with another embodiment of the pharmaceutical compositions of the present invention, the water-soluble active ingredient comprises levetiracetam.

In accordance with another embodiment of the pharmaceutical composition of the present invention, the polymer component includes between about 0% and 40% of a water-soluble polymer.

In accordance with another embodiment of the pharmaceutical composition of the present invention, the water-soluble active ingredient has a water solubility of at least 10 mg/ml, and preferably at least 33 mg/ml.

In accordance with another embodiment of the pharmaceutical composition of the present invention, the water-insoluble polymer is a polymer such as ethyl cellulose, butyl cellulose, cellulose acetate, cellulose acetate butyrate, ethylene vinyl acetate copolymer, polyvidone acetate, polyvinyl acetate, polyvinyl butyrate, polymethacrylate, ammonia methacrylate copolymer, and mixtures thereof. Preferably, the water-insoluble polymer comprises ethylcellulose, polymethacrylates, or ammonia methacrylate copolymer, most preferably ethylcellulose.

In accordance with another embodiment of the pharmaceutical composition of the present invention, the water-insoluble polymer comprises from between about 4 and 20 wt. % of the tablet core. In a most preferred embodiment, the water-insoluble polymer comprises about 12 wt. % of the tablet core.

In accordance with another embodiment of the pharmaceutical composition of the present invention, the extended release coating comprises from about 1 to 20 wt. % of the pharmaceutical composition. Preferably, the extended release coating comprises from about 2 to 10 wt. % of the pharmaceutical composition, and in a most preferred embodiment, about 6 wt. % of the pharmaceutical composition.

In accordance with one embodiment of the pharmaceutical composition of the present invention, the water-soluble polymer in the extended release coating is methylcellulose, hydroxypropylcellulose, hydroxypropylmethylcellulose, polyvinyl pyrrolidone, polyvinyl alcohol, polyethylene glycol, and the like.

In a preferred embodiment, the water-soluble polymer is hypromellose(hydroxypropylmethylcellulose).

In accordance with another embodiment of the pharmaceutical composition of the present invention, the ratio of the water-soluble polymer to the water-insoluble polymer in the extended release coating ranges from 10:90 to 90:10, and preferably from 30:70 to 70:30.

BRIEF DESCRIPTION OF THE DRAWINGS

The present invention may be more fully appreciated with reference to the following detailed description, which in turn refers to the Figures, in which.

DETAILED DESCRIPTION

Figure 1:
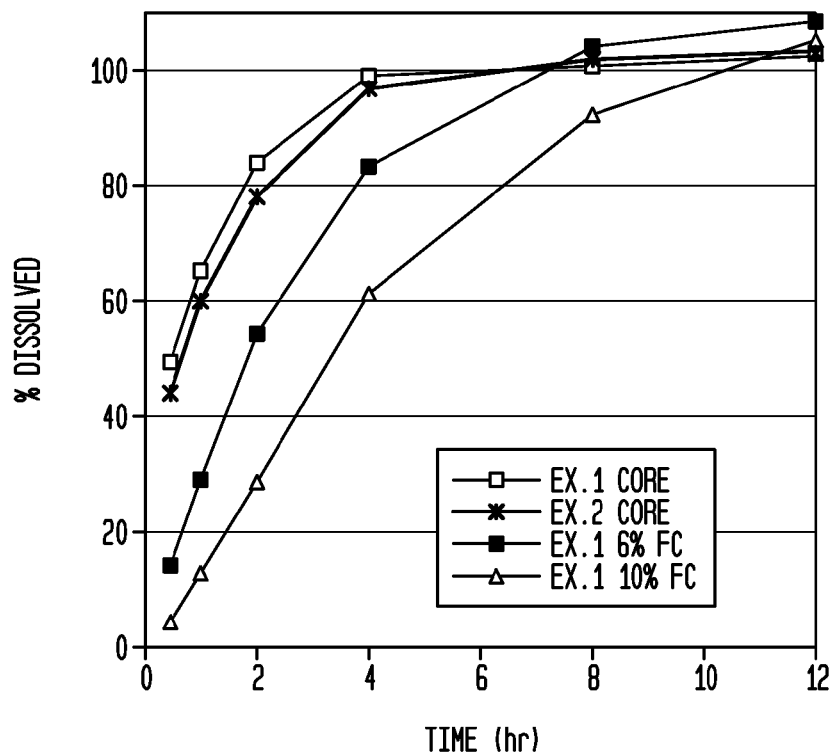
FIG. 1 is a graphical representation of the dissolution characteristics of extended release tablets in accordance with the present invention.

The pharmaceutical compositions of the present invention comprise a tablet for extended release of a water-soluble active ingredient in the form of a tablet core which includes both the water-soluble active ingredient and a polymer component, which comprises a water-insoluble polymer. In a preferred embodiment of this invention, the polymer component can be solely made up of a water-insoluble polymer, or can consist essentially of a water-insoluble polymer. On the other hand, it is also within the scope of the present invention that the water-insoluble polymer can comprise between about 60 and 100 wt. %, preferably 80 and 100 wt. %, and most preferably between about 90 and 100 wt. % of the polymer component in the tablet core. These pharmaceutical compositions can also include an extended release coating over the tablet core, preferably including a combination of at least one water-insoluble polymer and at least one water-soluble polymer.

The tablet core of the present invention is produced by wet granulation and compression of the core ingredients. The use of top-spray fluid bed granulation is preferred. While these primarily include the water-soluble active ingredient and the polymer components discussed above, the core can also include other ingredients such as binders and other materials known to those of ordinary skill in this art. These can include diluents, lubricants, anti-adherents, glidants, and the like.

The tablet preparation can use either wet or dry granulation techniques. Dry granulation techniques involve mixing the drug with a binder or directly with the water-insoluble polymer, or both, followed by slug formation on a tablet press or using roll compactors. Wet granulation, on the other hand, includes aqueous or non-aqueous granulation and in which the wet granulation process includes mixing the active ingredient with a diluent or mixture of diluents as well as the water-insoluble polymer. Granulation of the blend with the binder mass then takes place to form the wet mass, followed by drying and sizing. The binder may optionally be mixed with the dry blend and granulation performed with aqueous or non-aqueous solvents. Solvents for non-aqueous granulation include, for example, ethanol, isopropyl alcohol and dichloromethane.

In a preferred embodiment of the present invention, levetiracetam is used as the water-soluble active ingredient, and is granulated using non-aqueous granulation techniques. Most particularly, it is preferred that the active ingredient be mixed in a fluid bed with a diluent such as lactose, which is then sprayed with a non-aqueous solution, such as ethylcellulose. The granules are then dried and blended with additional ingredients, including ingredients such as colloidal silicon dioxide, magnesium stearate, sodium lauryl sulfate, and the like. This blend is then compressed into tablets.

The essential component of the pharmaceutical composition of the present invention is the core containing the active ingredient. The active ingredient in this case is a highly water-soluble drug having a water solubility of at least 10 mg/ml, preferably at least 33 mg/ml. The most preferred water-soluble drug is levetiracetam. In the case of the present invention, the desired extended release characteristics are primarily controlled by the use of a polymer substance which is a water-insoluble polymer in combination with the pharmaceutical ingredient itself in the tablet core. The use of a water-insoluble polymer in the core is thus a critical element of the present invention. More particularly, it is preferred that the substantially water-insoluble polymer comprise substantially the only polymer used in the tablet core, preferably at least about 60 wt. % of the total polymer content, more preferably between about 70 wt. % and 100 wt. % of the polymer content, and even more preferably between about 90 wt. % and 100 wt. % of the total polymer content, and in a preferred embodiment all of the polymer used in the tablet core comprises a substantially water-insoluble polymer.

Among the water-insoluble polymers which are preferred for use in connection with the present invention are cellulose ethers such as ethylcellulose, butylcellulose, cellulose acetate, cellulose acetate butyrate, ethylene vinyl acetate copolymer, polyvidone acetate, polyvinyl acetate, polyvinyl butyrate, polymethacrylates, including ethylacrylate/methylmethacrylate copolymers, and ammonia methacrylate copolymers, thus including commercially available dispersions of film-formers such as Eudragit RLX30D, Eudragit NE30D, and Eudragit RS30D. Preferably, the extended release agent forming the polymer in the tablet core comprises ethylcellulose.

The amount of water-insoluble polymer contained in the tablet core of the pharmaceutical compositions of the present invention will generally comprise from about 1% w/w to 50% w/w of the extended release core, preferably from about 4% w/w to 20% w/w of the extended release tablet core, and most preferably about 12% w/w of the tablet core.

While the tablet core of the present invention must include a polymer which is primarily the water-insoluble polymer as discussed above, it is possible to utilize some amount of a water soluble or hydrophilic polymer in combination with the critical water-insoluble polymers of the present invention. Thus, the tablet core includes an overall polymer component which can include from about 0 wt. % to 40 wt. % of a water-soluble polymer, preferably from 0 wt. % to 20 wt. %, of a water-soluble polymer, and most preferably between 0 wt. % to 10 wt. %, of a water-soluble polymer. These water-soluble polymers which can be included to the extent discussed above in the tablet core of the pharmaceutical compositions of this invention include polymers such as methylcellulose, hydroxypropylcellulose, hydroxypropylmethylcellulose, polyvinyl pyrrolidone, polyvinyl alcohol, hydroxyethylcellulose, and polyethylene glycols. In a most preferred embodiment, however, no effective amount of any water-soluble polymers is included in the tablet core.

In addition to the active pharmaceutical ingredient and the polymer composition, the core itself can include other components. Thus, inert diluents can be included in the core such as lactose, starch, and the like. Such inert diluents can be present in amounts of between about 0 wt. % to 50 wt. % of the tablet core, preferably from about 0 wt. % to 30 wt. % of the tablet core, and most preferably from about 2 wt. % to 20 wt. % of the tablet core. The tablet core can also include glidants such as corn starch, talc, calcium silicate, magnesium silicate, colloidal silicon dioxide, silicone hydrogel, and other materials known to those of ordinary skill in this art. The tablet core can also include anti-adherents, such as magnesium stearate, talc, calcium stearate, glyceryl behenate, polyethylene glycols, hydrogenated vegetable oil, mineral oil, stearic acid, and other such materials known to those of ordinary skill in this art. Finally, the tablet core can also include lubricants such as calcium stearate, magnesium stearate, sodium stearyl fumarate, glyceryl palmitostearate, glyceryl stearate, mineral oil, stearic acid and zinc stearate, and other minerals known to those of ordinary skill in this art. Preferably, the glidants, lubricants and anti-adherents can be present in the range of from about 0.5 wt. % to 10 wt. % of the tablet core and preferably in the range of from about 0.5 wt. % to 2 wt. % of the tablet core.

In a preferred embodiment of the present invention, an extended release coating is placed over the tablet core, preferably comprising a mixture of water-soluble and water-insoluble polymers such as those already discussed above. Such extended release coatings can comprise from between about 1 wt. % to 20 wt. % of the overall tablet itself, preferably from about 2 wt. % to 10 wt. % of the overall tablet itself. In a most preferred embodiment, the extended release coating is about 6 wt. % of the entire tablet. The water-soluble and water-insoluble polymers used in the extended release coating are the same water-soluble and water-insoluble polymers discussed above in connection with the tablet core itself. Selection of the specific ratio of water-soluble polymer to water-insoluble polymer in the extended release coating can thus affect the dissolution rate of the water-soluble drug, such as levetiracetam, from the core. In general, the ratio of the water-soluble to water-insoluble polymers in the extended release coating ranges from about 10:90 to 90:10, more preferably 30:70 to 70:30.

These extended release coatings can also include selected plasticizers for creating such film coatings which are less brittle in nature. These plasticizers include those known to those of skill in this art, such as acetyltributyl citrate, triacetin, acetyltriethyl citrate, dibutylphthalate, triethyl citrate, polyethylene glycol, propylene glycol, and mixtures thereof. Preferably, triethyl citrate is utilized. The amount of such plasticizer utilized in these extended release coatings is from about 0.01 to about 30 wt. % based on the total weight of the extended release coating, preferably from about 0.1 to about 15 wt. %

The extended release coatings can also include anti-tacking agents which are intended to prevent these films from becoming tacky and leading to undesirable agglomeration of the tablets. These anti-tacking agents can include, but are not limited to, adipic acid, magnesium stearate, calcium stearate, zinc stearate, hydrogenated vegetable oil, talc, sodium benzoate, sodium lauryl sulphate, magnesium lauryl sulphate, and mixtures thereof. In a preferred embodiment, talc is the anti-tacking agent.

The extended release coatings of the present invention can also include pigments or water-insoluble colors, such as iron oxide pigments, titanium dioxide, and aluminum lakes and the like. In a preferred embodiment, titanium dioxide is employed as the pigment.

The present invention may also be further understood with reference to the following examples:

EXAMPLES 1-4

TABLE 1

Examples of Levetiracetam Tablet Formulations

| | % w/w | | | |
|---|---|---|---|---|
| Ingredients | Example 1 | Example 2 | Example 3 | Example 4 |
| Core Formulation | | | | |
| Eudragit RS30D[1] | 8.0 | 16.0 | — | — |
| Eudragit NE30D[2] | — | — | 4.0 | 8.0 |
| Povidone K-29/32 | — | — | — | 2.86 |
| Talc | 2.4 | 4.8 | 1.2 | 2.4 |
| Levetiracetam | 71.43 | 71.43 | 71.43 | 71.43 |
| Lactose, Fast flo | 16.92 | 6.52 | 22.12 | 14.06 |
| Colloidal Silicon Dioxide | 0.25 | 0.25 | 0.25 | 0.25 |
| Magnesium Stearate/Sodium Lauryl Sulfate | 1.0 | 1.0 | 1.0 | 1.0 |
| Core Total | 100.0 | 100.0 | 100.0 | 100.0 |
| Coating Formulation | | | | |
| Surelease E-7-19010[3] | 7.0 | — | — | 9.0 |
| Hypromellose (Pharmacoat 603) | 3.0 | — | — | 1.0 |
| FC Total | 110.0 | — | — | 10.0 |

[1]Solids composed of ammonio methacrylate copolymer Type B, sorbic acid and sodium hydroxide.
[2]Solids composed of ethyl acrylate and methyl methacrylate copolymer and nonoxynol 100.
[3]Solids composed of ethylcellulose, ammonium hydroxide, medium chain triglyceride, oleic acid.

Example 1

A mixture of 1250.0 grams of levetiracetam and 296.1 grams of lactose was sprayed with a suspension (20% solids content) composed of 466.7 grams of Eudragit RS30D, 42.0 grams of talc, and 401.3 grams of water in a fluid bed. The resulting granules were dried in the fluid bed and milled, and 1512.5 grams of the milled granules were blended with 3.9 grams of colloidal silicon dioxide and 15.4 grams of magnesium stearate/sodium lauryl sulfate. This blend was then compressed into tablets. 300 grams of such cores were coated with a suspension of Surelease E-7-19010, hydroxypropylmethylcellulose and water (10% solids content). The product produced had the formulation of Example 1 shown in Table 1.

Example 2

Using the same process as used in Example 1, the formulation of Example 2 shown in Table 1 was produced, not including any extended release coating on the tablet core.

Example 3

Utilizing the same process set forth in Example 1, the formulation of Example 3 was obtained, again without using any extended release coating thereon.

Example 4

A mixture of 1250.0 grams of levetiracetam and 246.1 grams of lactose was sprayed with a solution of 50.0 grams of povidone in 300.0 grams of water in a fluid bed. The granules were cooled and sprayed with a suspension (20% solids content) composed of 466.7 grams of Eudragit NE30D, 42.0 grams of talc, and 401.3 grams of water. The resultant granules were milled, blended with colloidal silicon dioxide and magnesium stearate/sodium lauryl sulfate, and the blend was then compressed into tablets. The cores were then coated with a suspension of Surelease, hydroxypropylmethylcellulose and water (10% solids content). The samples were tested for dissolution at 6% and 10% coating weight gains.

The dissolution characteristics of the 500 mg extended release tablets prepared in Examples 1 and 2 including the 6% and 10% coating weight gains for the extended release coatings, were measured using USP Apparatus I at 100 rpm in a 6.8 pH buffer. The results are shown in FIG. 1

Figure 2:
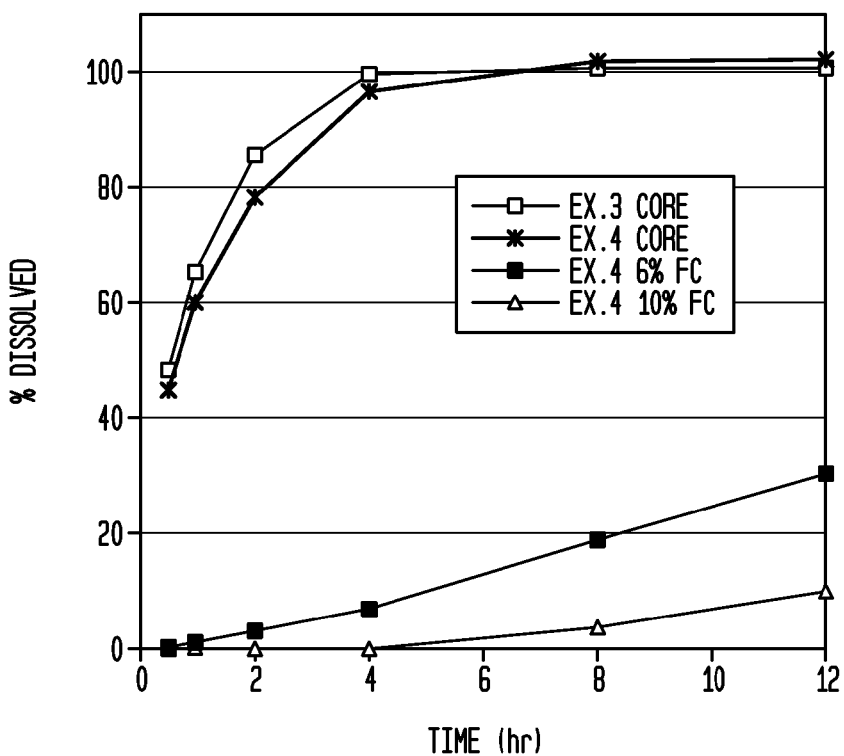
FIG. 2 is a graphical representation of the dissolution characteristics of additional extended release tablets in accordance with the present invention.

The dissolution characteristics of the 500 mg levetiracetam extended release tablets prepared in Examples 3 and 4 were measured using USP Apparatus I at 100 rpm in a 6.8 pH buffer and the results are set forth in FIG. 2.

EXAMPLES 5-7

TABLE 2

Examples of Levetiracetam Tablet Formulations

| | % w/w | | |
|---|---|---|---|
| Ingredients | Example 5 | Example 6 | Example 7 |
| Core Formulation | | | |
| Ethylcellulose, 10 cps | 7.5 | 12.0 | — |
| Ethylcellulose, 45 cps | — | — | 20.0 |
| Levetiracetam | 71.43 | 71.43 | 76.92 |
| Lactose, Fast flo | 19.57 | 15.07 | 1.58 |
| Colloidal Silicon Dioxide | 0.5 | 0.5 | 0.5 |
| Magnesium Stearate/Sodium Lauryl Sulfate | 1.0 | 1.0 | 1.0 |
| Core Total | 100.0 | 100.0 | 100.0 |
| Coating Formulation | | | |
| Surelease E-7-19010[1] | 4.20 | 4.80 | — |
| Hypromellose (Pharmacoat 603) | 1.80 | 1.20 | — |
| FC Total | 106.0 | 106.0 | — |

[1]Solids composed of ethylcellulose, ammonium hydroxide, medium chain triglyceride and oleic acid.

Example 5

A mixture of 1200.0 grams of levetiracetam and 328.8 grams of lactose was sprayed with a solution (9% solid content) composed of 126.0 grams of ethylcellulose and 1274.0 grams of alcohol in a fluid bed. The resultant granules were dried in the fluid bed and milled and the milled granules were then blended with colloidal silicon dioxide and magnesium stearate/sodium lauryl sulfate. The blend was then compressed into tablets. These cores were then coated with a suspension of Surelease, hydroxypropylmethylcellulose and water (10% solids). The formulation obtained is set forth in Table 2.

Example 6

Using the same process as set forth in Example 5, the formulation of Example 6 shown in Table 2 was obtained.

Example 7

Using the same process set forth in Example 5, the formulation of Example 7 was obtained, which included no extended release coating on the tablet cores.

Figure 3:
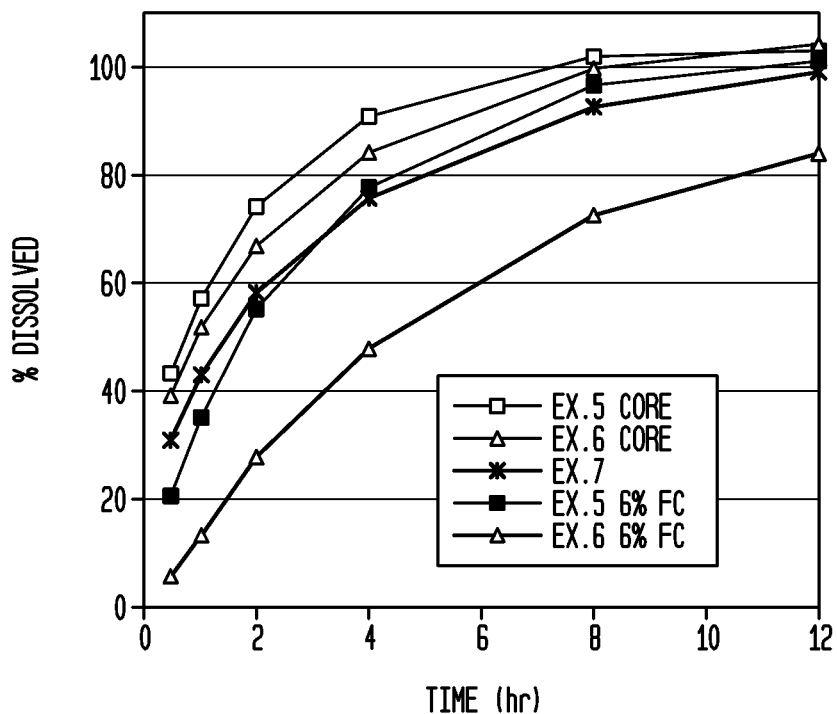
FIG. 3 is a graphical representation of the dissolution characteristics of additional extended release tablets in accordance with the present invention.

Referring to FIG. 3, the dissolution characteristics of the 500 mg levetiracetam extended release tablets were measured using USP Apparatus I at 100 rpm in a 6.8 pH buffer.

EXAMPLES 8 AND 9

TABLE 3

Examples of Levetiracetam Tablet Formulation

| | % w/w | | | | | |
|---|---|---|---|---|---|---|
| Ingredients | Example 8 | | | Example 9 | | |
| Core Formulation | | | | | | |
| Ethylcellulose, 10 cps | 12.0 | | | 12.0 | | |
| Levetiracetam | 83.3 | | | 83.3 | | |
| Lactose, Fast flo | 3.17 | | | 3.17 | | |
| Colloidal Silicon Dioxide | 0.5 | | | 0.5 | | |
| Magnesium Stearate/Sodium Lauryl Sulfate | 1.0 | | | 1.0 | | |
| Core Total | 100.0 | | | 100.0 | | |
| Coating Formulation | FC1 | FC2 | FC3 | FC1 | FC2 | FC3 |
| Surelease E-7-19010[1] | 4.62 | 4.38 | 3.90 | — | — | — |
| Ethylcellulose, 45 cps | — | — | — | 2.1 | 2.4 | 1.8 |
| Hypromellose (Pharmacoat 603) | 1.38 | 1.62 | 2.10 | 3.9 | 3.6 | 4.2 |
| FC Total | 106.0 | 106.0 | 106.0 | 106.0 | 106.0 | 106.0 |

[1]Solids composed of ethylcellulose, ammonium hydroxide, medium chain triglyceride and oleic acid.

Using the same process set forth in Example 5, the formulation of Example 8 in Table 3 was obtained.

Using the same process set forth in Example 5 to prepare the tablet core, the formulation listed in Example 9 in Table 3 was obtained. The cores were coated in this case with a solution of ethylcellulose and hydroxypropylmethylcellulose in alcohol (7% solids content).

Figure 4:
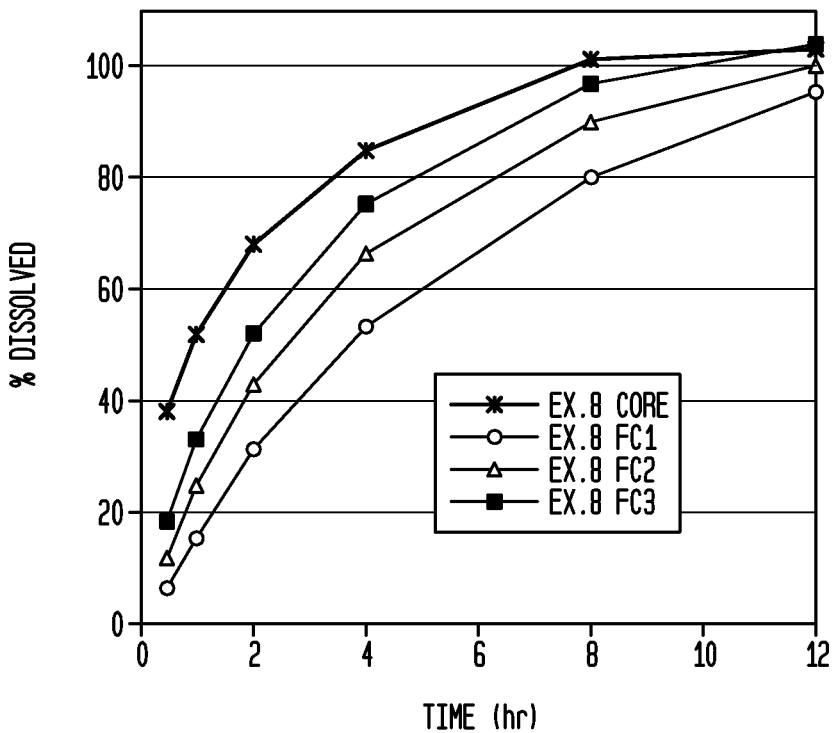
FIG. 4 is a graphical representation of the dissolution characteristics of additional extended release tablets in accordance with the present invention.
Figure 5:
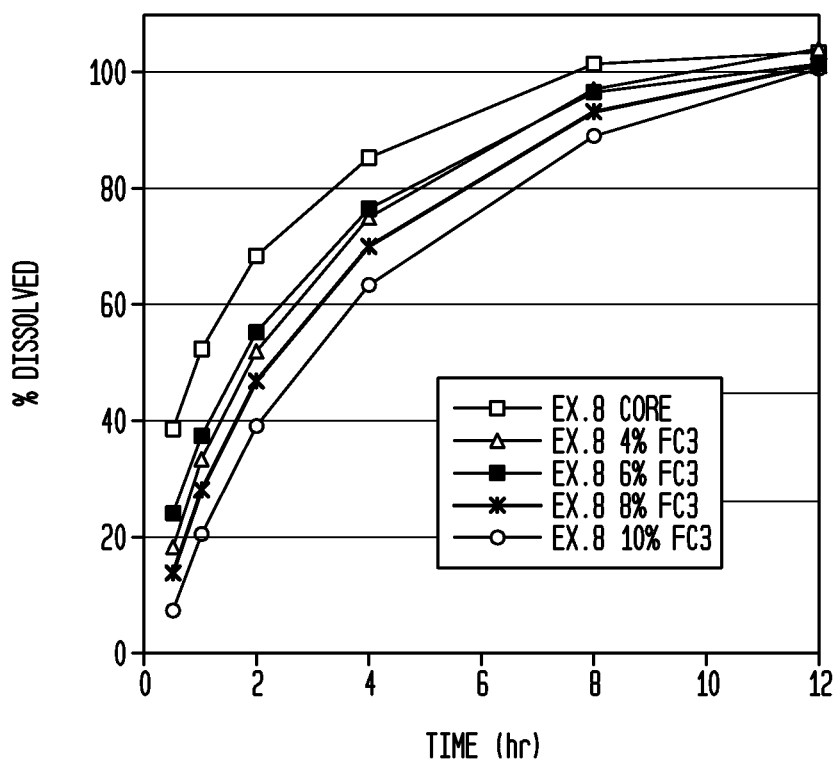
FIG. 5 is a graphical representation of the dissolution characteristics of additional extended release tablets in accordance with the present invention.
Figure 6:
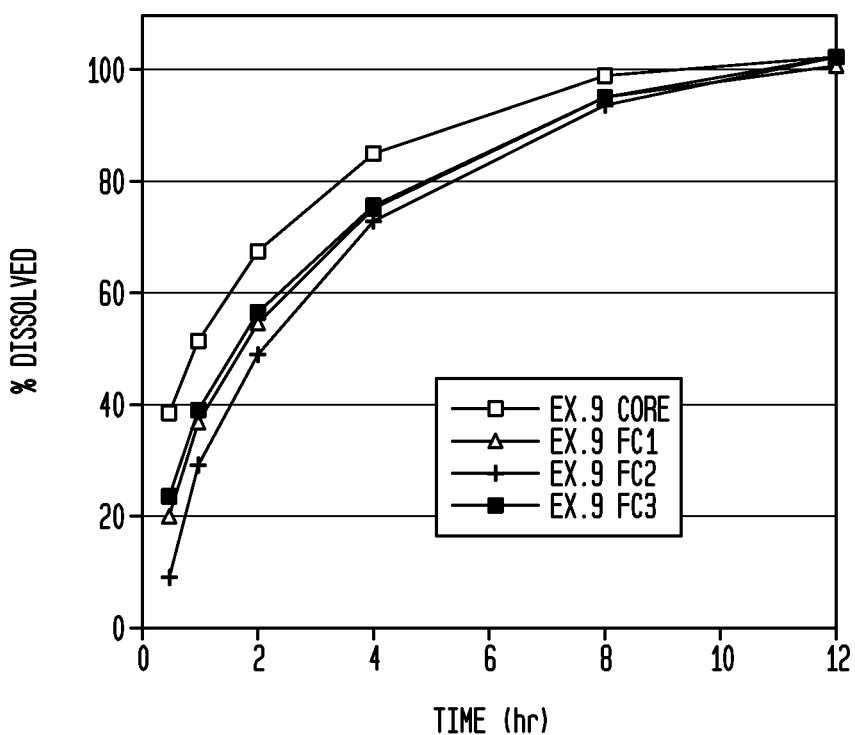
FIG. 6 is a graphical representation of the dissolution characteristics of additional extended release tablets in accordance with the present invention.

Referring to FIGS. 4-6, the dissolution characteristics of 500 mg levetiracetam extended release tablets were measured using USP Apparatus 1 at 100 rpm in 6.8 pH buffer.

FIG. 1 shows the dissolution curves of two tablet core formulations prepared with varying levels of Eudragit RS30D. As shown in FIG. 1, extended-release of a highly water soluble drug such as levetiracetam can be achieved with water-insoluble polymer levels of only 8% w/w. FIG. 1 also shows dissolution of an ethylcellulose coated tablet at a 30% hydroxypropylmethylcellulose level in the coating, and at two coating levels. As expected, the dissolution rate of levetiracetam can thus be further decreased by coating the core, and the rate of drug release can be controlled by the amount of coating on the core.

FIG. 2 shows the dissolution curves of two tablet core formulations prepared with varying levels of Eudragit NE30D. Again, extended-release of levetiracetam can be achieved with water-insoluble polymer levels of only 4% w/w. FIG. 2 also shows dissolution of an ethylcellulose coated tablet at a 10% hydroxypropylmethylcellulose level in the coating and at two coating levels. Again, the dissolution rate of levetiracetam can be further decreased by coating the core, and the rate of drug release could be controlled by the amount of coating on the core. A comparison of the dissolution of coated tablets in FIGS. 1 and 2 shows that the rate of drug release can be controlled by the amount of water soluble polymer in the ethylcellulose coating.

FIG. 3 shows the dissolution curves of three tablet core formulations prepared with varying levels of ethylcellulose. The rate of drug release from the tablet core decreased as the level of ethylcellulose content increased. FIG. 3 also shows dissolution of ethylcellulose cores coated with 6% w/w of ethylcellulose coatings at two levels of hydroxypropylmethylcellulose in the coating. As seen earlier, the dissolution rate of levetiracetam can be further decreased by coating the core, and the rate of drug release can be controlled by the amount of water soluble polymer in the coating.

FIG. 4 shows the dissolution curves of an ethylcellulose core coated with 6% w/w of an ethylcellulose coating, with varying amounts of hydroxypropylmethylcellulose in the coating. FIG. 6 shows the dissolution curves of ethylcellulose core coated with 6% w/w of a non-aqueous ethylcellulose coating with varying amounts of hypromellose in the coating. As seen earlier, the dissolution rate of levetiracetam can be further decreased by coating the core and the rate of drug release can be controlled by the amount of water soluble polymer in the coating.

FIG. 5 shows the effect of ethylcellulose coating level with 35% of water soluble polymer in the coating. As shown in FIG. 5, the rate of drug release could be decreased by increasing the amount of coating.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A pharmaceutical composition in the form of a tablet comprising a compressed tablet core comprising a water-soluble active ingredient comprising levetiracetam and a polymer component consisting essentially of a water-insoluble polymer comprising from between about 1 and 50 wt. % of said compressed tablet core, and comprising substantially the only polymer in said compressed tablet core, such that said compressed tablet core is free of any water-soluble polymer.

2. The pharmaceutical composition of claim 1 wherein said water-insoluble polymer comprises from between about 4 and 20 wt. % of said compressed tablet core.

3. The pharmaceutical composition of claim 2 wherein said water-insoluble polymer comprises about 12 wt. % of said compressed tablet core.

4. The pharmaceutical composition of claim 1 including an extended release coating surrounding said compressed tablet core.

5. The pharmaceutical composition of claim 4 wherein said extended release coating comprises from about 1 to 20 wt. % of said pharmaceutical composition.

6. The pharmaceutical composition of claim 5 wherein said extended release coating comprises from about 2 to 10 wt. % of said pharmaceutical composition.

7. The pharmaceutical composition of claim 6 wherein said extended release coating comprises about 6 wt. % of said pharmaceutical composition.

8. The pharmaceutical composition of claim 4 wherein said extended release coating includes a water-insoluble polymer selected from the group consisting of ethylcellulose, butylcellulose, cellulose acetate, cellulose acetate butyrate, ethylene vinyl acetate copolymer, polyvidone acetate, polyvinyl acetate, polyvinyl butyrate, polymethacrylate, ammonia methacrylate copolymer, and mixtures thereof.

9. The pharmaceutical composition of claim 8 wherein said water-insoluble polymer in said extended release coating comprises ethylcellulose.

10. The pharmaceutical composition of claim 4 wherein said extended release coating includes a water-soluble polymer selected from the group consisting of methylcellulose, hydroxypropylcellulose, hydroxypropylmethylcellulose, polyvinyl pyrrolidone, polyvinyl alcohol, polyethylene glycol, and mixtures thereof.

11. The pharmaceutical composition of claim 10 wherein said water-soluble polymer in said extended release coating comprises hydroxypropylmethylcellulose.

12. The pharmaceutical composition of claim 4 wherein said extended release coating includes a water-soluble polymer and a water-insoluble polymer, and wherein the ratio of said water-soluble polymer to said water-insoluble polymer in said extended release coating ranges from 10:90 to 90:10.

13. The pharmaceutical composition of claim 12 wherein the ratio of said water-soluble polymer to said water-insoluble polymer in said extended release coating is from 30:70 to 70:30.

14. The pharmaceutical composition of claim 1 wherein said water-insoluble polymer is selected from the group consisting of ethyl cellulose, butyl cellulose, cellulose acetate, cellulose acetate butyrate, ethylene vinyl acetate copolymer, polyvidone acetate, polyvinyl acetate, polyvinyl butyrate, polymethacrylate, ammonia methacrylate copolymer, and mixtures thereof.

15. The pharmaceutical composition of claim 14 wherein said water-insoluble polymer is selected from the group consisting of ethylcellulose, polymethacrylates, ammonia methacrylate copolymer, and mixtures thereof.

16. The pharmaceutical composition of claim 15 wherein said water-insoluble polymer comprises ethylcellulose.

17. The pharmaceutical composition of claim 16 wherein said levetiracetam is present in an amount of about 83.3 wt. % of said compressed tablet core.

18. The pharmaceutical formulation of claim 16 wherein said compressed tablet core includes an inert diluent.

19. The pharmaceutical composition of claim 18 wherein said inert diluent comprises lactose.

20. The pharmaceutical composition of claim 19 wherein said lactose is present in an amount of between about 2 wt. % and 20wt. % of said core.

21. The pharmaceutical composition of claim 16 wherein said compressed tablet core includes a lubricant.

22. The pharmaceutical composition of claim 21 wherein said lubricant comprises magnesium stearate.

23. The pharmaceutical composition of claim 22 wherein said magnesium stearate is present in an amount of between about 0.5 wt. % and 2 wt. % of said compressed tablet core.

24. The pharmaceutical composition of claim 16 wherein said compressed tablet core includes a glidant.

25. The pharmaceutical composition of claim 24 wherein said glidant comprises colloidal silicon dioxide.

26. The pharmaceutical composition of claim 16 wherein said ethylcellulose comprises from between about 4 wt. % and 20 wt. % of the compressed tablet core.

27. The pharmaceutical composition of claim 26 wherein said ethylcellulose comprises about 12 wt. % of said compressed tablet core.

28. The pharmaceutical composition of claim 27 wherein said compressed tablet core includes an inert diluent comprising lactose, in an amount of between about 2 wt. % and 20 wt. % of said core.

29. The pharmaceutical composition of claim 28 wherein said compressed tablet core includes a lubricant comprising magnesium stearate in an amount between about 0.5 wt. % and 2 wt. % of said compressed tablet core.

30. The pharmaceutical composition of claim 29 wherein said compressed tablet core includes a glidant comprising colloidal silicon dioxide.

* * * * *